(12) United States Patent
Izu et al.

(10) Patent No.: US 7,236,083 B2
(45) Date of Patent: Jun. 26, 2007

(54) RESISTANCE TYPE OXYGEN SENSOR AND OXYGEN SENSOR DEVICE USING IT AND AIR/FUEL RATIO CONTROL SYSTEM

(75) Inventors: Noriya Izu, Aichi (JP); Woosuck Shin, Aichi (JP); Norimitsu Murayama, Aichi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 184 days.

(21) Appl. No.: 10/517,771

(22) PCT Filed: Jun. 25, 2003

(86) PCT No.: PCT/JP03/08052

§ 371 (c)(1),
(2), (4) Date: Dec. 27, 2004

(87) PCT Pub. No.: WO2004/003536

PCT Pub. Date: Jan. 8, 2004

(65) Prior Publication Data

US 2005/0236271 A1  Oct. 27, 2005

(30) Foreign Application Priority Data

Jun. 27, 2002 (JP) ............................. 2002-188650
Jul. 8, 2002 (JP) ............................. 2002-199022
Nov. 20, 2002 (JP) ............................. 2002-335912

(51) Int. Cl.
*H01C 7/00* (2006.01)
(52) U.S. Cl. ........................................ 338/34; 73/23.1
(58) Field of Classification Search ................. 338/34, 338/325–328; 73/23.21, 31.06; 204/274, 204/431; 205/785; 501/103, 126; 502/217, 502/304; 423/213.2, 263
See application file for complete search history.

(56) References Cited

U.S. PATENT DOCUMENTS 4,001,756 A * 1/1977 Heijne ..................... 338/34

(Continued)

FOREIGN PATENT DOCUMENTS

DE          42 10 397          10/1993

(Continued)

OTHER PUBLICATIONS

Esper, M.J. et al. "Titania Exhaust Gas Sensor for Automotive Applications", SAE Technical Paper Series, 790140, pp. 1-9 1979.

(Continued)

*Primary Examiner*—Tu Hoang
(74) *Attorney, Agent, or Firm*—Oblon, Spivak, McClelland, Maier & Neustadt, P.C.

(57) ABSTRACT

The present invention provides a resistance-type oxygen sensor, and an oxygen sensor device and an air/fuel ratio control system using same. The present invention relates to a resistance-type oxygen sensor with suppressed temperature dependence, wherein: (1) a gas detection unit composed of an oxide semiconductor with a resistance value varying according to temperature and the oxygen partial pressure of atmospheric gas and a temperature compensation unit composed of a conductor with suppressed dependence of a resistance value on oxygen partial pressure are connected in series; (2) the temperature compensation unit is composed of an oxygen ion conductor; and (3) an electrode for electric contact with the temperature compensation unit is exposed to the atmospheric gas and is a porous body; an oxygen sensor device and an air/fuel ratio control system.

19 Claims, 12 Drawing Sheets

U.S. PATENT DOCUMENTS

| | | | |
|---|---|---|---|
| 4,147,513 A * | 4/1979 | Bienkowski et al. | 338/34 |
| 4,225,842 A * | 9/1980 | Schlesselman et al. | 338/34 |
| 4,387,359 A * | 6/1983 | Tien et al. | 338/34 |
| 4,519,237 A * | 5/1985 | Kubo | 73/23.21 |
| 4,574,264 A * | 3/1986 | Takahashi et al. | 338/34 |
| 4,659,435 A * | 4/1987 | Brothers et al. | 204/274 |
| 6,150,299 A * | 11/2000 | Umemoto et al. | 502/304 |
| 6,375,828 B2 * | 4/2002 | Ando et al. | 205/781 |
| 2005/0236271 A1 | 10/2005 | Izu et al. | |
| 2006/0057048 A1 * | 3/2006 | Chan et al. | 423/263 |
| 2006/0081473 A1 * | 4/2006 | Izu et al. | 204/431 |

FOREIGN PATENT DOCUMENTS

| | | |
|---|---|---|
| DE | 42 10 398 | 10/1993 |
| EP | 0 464 243 | 1/1992 |
| EP | 0 464 244 | 1/1992 |
| JP | 55-137334 | 10/1980 |
| JP | 58-024850 | 2/1983 |
| JP | 58-092946 | 6/1983 |
| JP | 59-027253 | 2/1984 |
| JP | 61-093944 | 5/1986 |
| JP | 62-174644 | 7/1987 |
| JP | 03-103760 | 4/1991 |
| JP | 03-267517 | 11/1991 |
| JP | 06-222026 | 8/1994 |
| JP | 07-063719 | 3/1995 |
| JP | 10-505164 | 5/1998 |
| JP | 2003-149189 | 5/2003 |

OTHER PUBLICATIONS

Varhegyi, E.B. et al. "Auger and SIMS study of segregation and corrosion behaviour of some semiconducting oxide gas-sensor materials", Sensors and Actuators B, vol. 18-19, pp. 569-572 1994.

Tan, Guo-Long et al. "Electronic conductivity of a ZrO2 thin film as an oxygen sensor", Thin Solid Films, vol. 330, pp. 59-61 1998.

U.S. Appl. No. 11/252,721, filed Oct. 19, 2005, Izu et al.

* cited by examiner

1 ··· SUBSTRATE
2 ··· ELECTRODE
3 ··· GAS DETECTION UNIT (OXIDE SEMICONDUCTOR)
4 ··· TEMPERATURE COMPENSATION UNIT
        (OXYGEN ION CONDUCTOR)

US 7,236,083 B2

RESISTANCE TYPE OXYGEN SENSOR AND OXYGEN SENSOR DEVICE USING IT AND AIR/FUEL RATIO CONTROL SYSTEM

TECHNICAL FIELD

The present invention relates to a resistance-type oxygen sensor with suppressed temperature dependence, and more particularly to a resistance-type oxygen sensor with suppressed temperature dependence, which has a gas detection unit composed of an oxide semiconductor having resistance varying according to the oxygen partial pressure in an atmospheric gas. The present invention is useful in providing a novel oxygen sensor device capable of measuring the oxygen partial pressure with a high accuracy and advantageously suitable, for example, for air/fuel ratio feedback control systems for controlling the air/fuel ratio of combustion engines for automobiles with the object of increasing the exhaust gas purification ratio or improving fuel consumption.

Further, the present invention also relates to a resistance-type oxygen sensor with greatly improved response rate, and more particularly to a novel resistant-type oxygen sensor which has a gas detection unit composed of an oxide semiconductor having resistivity varying according to the oxygen partial pressure in an atmospheric gas, this sensor enabling a significant reduction in the response time.

The present invention is useful in providing a novel oxygen sensor capable of measuring the oxygen partial pressure with a high accuracy and suitable, for example, for air/fuel ratio feedback control systems for controlling the air/fuel ratio of exhaust gas, mainly in automobiles or the like, with the object of increasing the exhaust gas purification ratio or improving fuel consumption.

BACKGROUND ART

The problem associated with the conventional resistance-type oxygen sensors using oxide semiconductors was that the resistance of oxide semiconductor that is a gas detection unit shows strong dependence not only on the oxygen partial pressure, but also on temperature, which resulted in a very strong dependence of the sensor output on temperature.

The following four measures are known for realizing an oxygen-insensitive characteristic of the resistance, that is, a resistance characteristic that does not depend on oxygen partial pressure and is necessary for a temperature compensation unit of the sensor. Those measures are listed hereinbelow.

The first one was reported by M. J. Esper et al. (SAE Technical paper, 1979), 790140) who used a high-density titanium oxide as a temperature compensation unit insensitive to oxygen gas. In this case the problem is that the resistance is insensitive to oxygen within a short interval, but shows the dependence on oxygen partial pressure in a long interval.

Secondly, a gas sensor was reported (European Patent Applications Nos. 0464243 and 0464244) in which part of the gas detection unit was covered with a gas-impermeable layer, thereby making the temperature compensation unit insensitive to oxygen gas. In this case the problem is that hair cracking occurs in the gas-impermeable layer covering part of the gas detection unit under the effect of degradation with time of thermal shocks, and gas permeates through the layer.

Thirdly, a method was described (German Patents No. 4210397 and 4210398) by which a gas-insensitive unit was obtained by doping metal atoms, for example, gold to the degree ensuring the loss of gas dependence. The drawback of this method is that the unit doped with metal atoms lacks stability.

Fourthly, in the initial report a mixture of p-type and n-type oxygen semiconductors was used as the temperature compensation unit (Japanese Patent Application Laid-open No. H6-222026) and a system was used in which thin films of p-type and n-type oxide semiconductors were used (Japanese Tokuhyo No. H10-505164). However, the problem associated with such temperature compensation units was that the p-type and n-type oxide semiconductors reacted in the operation temperature range of the sensor and long-term stability could not be obtained and that cracks appeared due to the difference in a thermal expansion coefficient between those materials.

Furthermore, when p-type and n-type oxide semiconductors are stacked in the gas-insensitive unit, the thin film formation conditions have to be accurately controlled to stack the films with good matching. On the other hand, when a mixture of p-type and n-type oxide semiconductors was produced, the problem was that the mixing process had to be controlled so as to obtain the desirable dispersion of the two oxide semiconductors. As a result, the process for producing the gas-insensitive unit was complex.

Furthermore, none of the aforementioned documents indicated that the temperature compensation unit does not depend on the oxygen partial pressure, or when such as indication was provided, the range of oxygen partial pressure was of two orders of magnitude. Within the framework of the above-described conventional technology, it is possible to suppose that in principle the range in which the resistance of the temperature compensation unit does not depend on oxygen partial pressure is small. More specially, in p-type semiconductors, the resistance, r, is proportional to $-1/n$ power of oxygen partial pressure P, and in n-type semiconductors, r is proportional to $1/n$ power of P. Here, n is from 4 to 6. If an equivalent circuit is considered, then in the case of a parallel circuit, the changes have to be as shown in FIG. 1, and in the case of a serial circuit, the changes have to be as shown in FIG. 2. Therefore, yet another problem is that if the range without dependence on oxygen partial pressure is small and the oxygen partial pressure shifts from this range, then the dependence of sensor output on oxygen partial pressure becomes extremely small. Furthermore, none of the aforementioned documents indicates that the output of the oxygen sensor does not depend on temperature or that temperature dependence is small.

On the other hand, for example solid-electrolyte sensors have been mainly used as oxygen sensors for automobiles (Japanese Patent Application Laid-open No. S55-137334). In the sensors of this type, the difference in oxygen partial pressure between a standard electrode and measurement electrode was measured as an electromotive force and it was necessary to use the standard electrode. The resultant problem was that the structure was complex and difficult to miniaturize. In order to resolve this problem, for example, a resistance-type oxygen sensor, which required no standard electrode, was disclosed (Japanese Patent Application Laid-open No. S62-174644). Explaining the measurement principle of the resistance-type oxygen sensor, first, the concentration of oxygen vacancies in an oxide semiconductor changes when the oxygen partial pressure of the atmosphere changes. There is a one-to-one correspondence between the resistivity or electron conductivity of oxide semiconductors and the concentration of oxygen vacancies, and the resistivity of the oxide semiconductor changes with changes in the concentration of oxygen vacancies. The oxygen partial pressure of the atmosphere can be determined by measuring the resistivity.

The problem associated with the resistance-type oxygen sensor was that the output had poor response when the oxygen partial pressure changed (Japanese Patent Application Laid-open No. H07-63719). Another problem was that titanium oxide was used as the oxide semiconductor of the resistance-type oxygen sensor, but this material had poor endurance and stability. In order to resolve the above-described problems, the inventors have conducted research and development of a resistance-type oxygen sensor using cerium oxide as the oxide semiconductor. Cerium oxide is known to have good endurance in corrosive gas atmosphere (E. B. Varhegyi et al., Sensors and Actuator, B, 18–19 (1994) 569). The response characteristic was improved by reducing the particle size of cerium oxide to 200 nm in the resistance-type oxygen sensor using cerium oxide (Japanese Patent Application No. 2002-240360).

However, even in this sensor, the response rate was not sufficiently high and had to be further improved. Other problems were that in this sensor, the electric conductivity of cerium oxide serving as the oxide semiconductor was low, that is, the resistivity was high and the dependence of electric conductivity (output) on the oxygen partial pressure decreased with the decrease in the operation temperature of the sensor. Those problems also had to be resolved.

Further, a sensor was also reported which used an oxide containing cerium ions and zirconium ions at a ratio of the amount of zirconium ions to the total amount of cerium ions and zirconium ions (referred to hereinbelow as "zirconium ion concentration") of 80 mol % or higher (Guo-Long Tan et al. Thin Solid Films 330 (1998) 59–61). However, the detection principle of those sensors was based on using an oxygen concentration increase/decrease cell which measures the difference between the oxygen partial pressure of the reference electrode and measurement electrode as an electromotive force.

DISCLOSURE OF THE INVENTION

With the foregoing in view, the inventors have conducted a comprehensive study in order to resolve the problems inherent to the conventional technology and to provide an oxygen sensor that can be fabricated by a simple process, has a temperature compensation unit with an electric resistance which is not sensitive to oxygen, has high resistance to thermal shocks and endurance, and demonstrates no sensitivity with respect to oxygen in a wide range of oxygen partial pressure. The results of this study demonstrate that the desired object can be attained by constructing the temperature compensation unit from an oxygen ion conductor that features a very small dependence of electric resistance value on oxygen partial pressure, exposing an electrode for electric contact with the temperature compensation unit to the atmospheric gas and making it from a porous material. This finding led to the creation of the present invention.

Thus, in accordance with the first aspect of the present invention, it is an object to provide a resistance-type oxygen sensor which has a gas detection unit composed of an oxide semiconductor with an electric resistance varying according to temperature and the oxygen partial pressure of the atmospheric gas and a temperature compensation unit with an electric resistance depending on temperature by showing no dependence on oxygen partial pressure, the temperature compensation unit being connected in series with the gas detection unit. It is another object of the present invention to provide a resistance-type oxygen sensor mainly suitable for measuring the partial pressure of oxygen gas in the exhaust gas of an automobile, the sensor comprising a temperature compensation unit based on the principle different from that of the conventional technology, wherein an electrode for electric contact with the temperature compensation unit is exposed to the atmospheric gas and is porous. It is yet another object of the present invention to provide a resistance-type oxygen sensor which can be fabricated by a simple process, has high resistance to thermal shocks, has high endurance, can be used as an oxygen sensor in a wide range of oxygen partial pressure, and has a low dependence of output on temperature.

Further, in the process of conducting the comprehensive study with the object of resolving the problems inherent to the conventional technology and improving significantly, mainly, the response rate of the sensor, the inventors have discovered that the desired object can be attained with a resistance-type oxygen sensor with an oxygen gas detection unit composed of an oxide semiconductor, wherein an oxide comprising cerium ions and zirconium ions at a specific concentration is used as the oxide semiconductor. The present invention was created based on the accumulated results of those research.

According to the second aspect in accordance with the present invention, it is an object to provide a resistance-type oxygen sensor having an oxygen gas detection unit using an oxide comprising cerium ions as the main component and having a short response time of the output related to changes in oxygen partial pressure, this response time being shorter than that of a resistance-type oxygen sensor in which an oxygen gas detection unit is composed only of cerium oxide. It is yet another object of the present invention to provide an oxygen sensor device suitable for a air/fuel ratio feedback control system for optimizing the combustion efficiency in combustion engines.

The first aspect of the present invention will be described below in greater detail.

The present invention relates to a resistance-type oxygen sensor in which a gas detection unit with an electric resistance depending on oxygen partial pressure and temperature and a temperature compensation unit with an electric resistance depending only on temperature are arranged on a substrate, for example, as shown in FIG. 3. The arrangement of the gas detection unit and temperature compensation unit on the substrate is not limited to that shown in FIG. 3. For example, (1) the gas detection unit may be disposed on the front surface of the substrate and temperature compensation unit may be disposed on the rear surface; (2) the arrangement can be reversed with respect to that of (1). The gas detection unit and temperature compensation unit are preferably in the form, for example, of thin films or thick films. Furthermore, it is preferred that the electric resistance of the gas detection unit and temperature compensation unit be as close to each other as possible. The resistance of each film can be controlled by changing the film size. Furthermore, the electrode structure is not limited to that shown in FIG. 3 and, for example, a structure of a crossed finger type is also possible. In the configuration shown in FIG. 3, the electrodes, which are in contact with the gas detection unit are disposed above the gas detection unit, but they can be also disposed between the substrate and gas detection unit. As for the mutual arrangement of the temperature compensation unit and electrodes, the substrate—thick film—porous electrode configuration is preferred. This is because the $O^{2-}=\frac{1}{2}O_2+2e^-$ reaction proceeds on the three-phase boundaries of the electrode, thick film, and gas, and if this reaction does not occur, the resistance of ion conductor increases. However, the substrate—electrode—thick film configuration is also possible, because the three-phase boundary is present if the thick film is porous.

Examples of materials for the substrate include aluminum oxide, magnesium oxide, and quartz, which are insulators, but those examples are not limiting. An oxide semiconductor represented by cerium oxide, titanium, and gallium oxide is used for the gas detection unit. An oxygen ion conductor with a temperature dependence close to that of the gas detection unit, for example, yttria-stabilized zirconia and gallium-doped ceria, is used for the temperature compensation unit. Cerium oxide is an oxide semiconductor, by with certain type of added metal ions, cerium oxide can become an oxygen ion conductor. More specifically, cerium oxide becomes an oxygen ion conductor if ions of a metal with a valence of two or three are added.

Further, when cerium oxide is used as the main component of the oxide semiconductor or oxygen ion conductor, the temperature dependence thereof can be appropriately varied by changing the type and amount of ions that are added. Therefore, an oxide comprising cerium oxide as the main component can be advantageously used for the gas detection unit and temperature compensation unit in accordance with the present invention. The temperature dependence can be controlled by changing the type and amount of ions that are added and a resistance-type oxygen sensor with a very small temperature dependence can be fabricated. Examples of materials for the electrodes include noble metals such as Pt and Pd and conductive oxides, but those examples are not limiting. The electrode that is in contact with the oxygen ion conductor serving as the temperature compensation unit has to be in the form of a porous body. If it is a dense body, then the $O^{2-}=\frac{1}{2}O_2+2e^-$ reaction does not proceed and the electric resistance of ion conductor serving as the temperature compensation unit changes even if the temperature is constant. In other words, the long-term stability is lost. For this reason, the electrode has to be a porous body. The electrode that is in contact with the gas detection unit may be in the form other than that of a porous body, but in order to produce it together with the electrode that is in contact with the temperature compensation unit, it is preferably also a porous body identical to that of the electrode that is in contact with the temperature compensation unit. This is because, in order to obtain different properties for the electrode that is in contact with the temperature compensation unit and the electrode that is in contact with the gas detection unit, one step is added to the manufacturing process and the production cost increases accordingly. Therefore, it is preferred that the electrodes for contact with the temperature compensation unit and gas detection unit be porous bodies.

The method for the fabrication of the sensor will be described below. First, the gas detection unit and temperature compensation unit are fabricated. Examples of the fabrication methods suitable in the case of thin films include sputtering, MOCVD, and sol-gel process, but those examples are not limiting. With those methods, thin films are fabricated on the substrate. Once the films have been formed, firing is conducted in air at a temperature of 1000–1200° C. In the case of thick films, an oxide semiconductor powder is first produced. Examples of methods suitable for this process include spray pyrolysis, spray dry method, and precipitation method, but those examples are not limiting. Then, the oxide semiconductor powder is mixed with an organic solvent such as a vehicle and squeeze oil, a paste is produced, and the paste is printed on the substrate. A screen printing method is preferably used as the printing method, but other methods may be also used.

Then heating is conducted in air at a temperature of 400–600° C., the organic solvent is removed, and firing is conducted in air at a temperature of 1000–1200° C.

The electrodes are then fabricated. Examples of methods suitable for this stage include a method for coating a noble metal paste, e.g., of Pt or Pd, by a screen printing method, and a method comprising sputtering of Pt and Pd, but those examples are not limiting. The screen printing method is preferred over the sputtering method as a method for forming a porous electrode because the screen printing method makes it possible to obtain a porous electrode in an easy manner. When the electrode is disposed between the substrate, gas detection unit, and temperature compensation unit, the electrode is fabricated on the substrate and then the gas detection unit and temperature compensation unit are fabricated thereupon.

In the case of a resistance-type oxygen sensor equipped with a heater, for example, a ceramic heater and a silicon microheater are mounted on the substrate. No specific limitation is placed on the mounting position, shape and characteristics of the heater. Because the resistance-type oxygen sensor in accordance with the present invention has small temperature dependence, the level of requirements placed on the heater is low and the performance of the heater is not important.

The resistance-type oxygen sensor in accordance with the present invention is used for an oxygen sensor device. Such a device can be freely designed by employing the resistance-type oxygen sensor in accordance with the present invention, an electric circuit unit, and a display unit for a sensor output as the basic structural elements. FIG. 4 shows an example of the electric circuit of such a device. In the figure, the circuit of the heater unit is omitted. The area in the figure that is surrounded with a dot line represents the resistance-type oxygen sensor. The oxygen sensor device can be fabricated by connecting the gas detection unit and temperature compensation unit in series, applying constant voltage, and reading the difference in potential in the gas detection unit as the sensor output.

The resistance-type oxygen sensor in accordance with the present invention, can be used, for example, in the air/fuel feedback control system for automobiles (including motorcycles) for controlling the air/fuel ratio. Here, the air/fuel ratio is the ratio of air and fuel and there is a one-to-one correspondence between the oxygen partial pressure and air/fuel ratio. Such a system can be freely designed by employing as the basic structural elements the resistance-type oxygen sensor in accordance with the present invention, a flow meter for measuring the flow rate of air flowing to the engine, a fuel injector for introducing fuel into the engine, and a control circuit for receiving signals from the oxygen sensor and flow meter, conducting calculations, and controlling the fuel injection rate of the fuel injector.

Furthermore, the resistance-type oxygen sensor in accordance with the present invention can be also used, for example, in an air/fuel feedback control system for optimizing the combustion efficiency of an combustion engine. Such a system can be freely designed by employing as the basic structural elements the resistance-type oxygen sensor in accordance with the present invention, a flow meter for measuring the flow rate of air flowing to the engine, a fuel controller for controlling the fuel introduced into the combustion engine, and an electronic control unit for receiving signals from the oxygen sensor and flow meter, conducting calculations, and sending an output signal to the fuel controller.

Further, the resistance-type oxygen sensor in accordance with the present invention can be also used, for example, in a system for detecting the exhaust gas catalyst degradation in automobiles. Such a system can be freely designed by employing as the basic structural elements the resistance-type oxygen sensor in accordance with the present invention, an electronic control unit for reading the signals from the oxygen sensor and determining as to whether the catalyst has degraded, and a display unit for receiving signals from the electronic control unit and displaying as to whether the catalyst has degraded.

The present invention provides a small resistance-type oxygen sensor of a simple structure which comprises a temperature compensation unit based on a novel principle that makes it possible to decrease greatly the dependence of output on temperature. Furthermore, the present invention also provides a resistance-type oxygen sensor suitable for a system for detecting the exhaust gas catalyst degradation in automobiles, this system making it possible to detect the degradation of catalysts for automobile exhaust gas purification. Moreover, the present invention also provides a resistance-type oxygen sensor suitable for an air/fuel ratio feedback control system for optimizing the combustion efficiency of a boiler.

If the electric resistance of a gas detection unit is denoted by $r_g$, then the $r_g$ can be represented by the following formula:

$$r_g = r_g^0 \times P^{1/n} \times \exp(E_g/kT)$$

Here, $r_g^0$ is a constant inherent to the gas detection unit, which depends neither on temperature nor on oxygen partial pressure, P is an oxygen partial pressure, n is a value from 4 to 6, $E_g$ is an activation energy of the gas detection unit, k is a Boltzman constant, T is a temperature. On the other hand, if the electric resistance of a temperature compensation unit is denoted by $r_n$, then $r_n = r_n^0 \times \exp(E_n/kT)$. Here, $r_n^0$ is a constant inherent to the temperature compensation unit, which depends neither on temperature nor on oxygen partial pressure, and $E_n$ is an activation energy of the temperature compensation unit.

If a constant voltage is applied, as shown in FIG. 4, then, the potential difference, $V_{out}$, in the gas detection unit will be represented by the following formula:

$$V_{out} = r_g/(r_g+r_n) \times V = r_g^0 \times P^{1/n} \times \exp(E_g/kT)/\{r_g^0 \times P^{1/n} \times \exp(E_g/kT) + r_n^0 \times \exp(E_n/kT)\} \times V.$$

If the activation energy of the gas detection unit is equal to that of temperature compensation unit, then $$V_{out} = r_g^0 \times P^{1/n}/(r_g^0 \times P^{1/n} \times r_n^0) \times V,$$

and the terms dependent on temperature are eliminated. In other words, the sensor output does not depend on temperature. When $E_g$ and $E_n$ are somewhat different, the output slightly depends on temperature. If the materials of the gas detection unit and temperature compensation unit are so selected that $E_g$ and $E_n$ are equal to each other, then a sensor can be obtained which shows absolutely no dependence on temperature.

A general specific feature of oxygen ion conductors is that the electric resistance does not depend on oxygen partial pressure in the range of oxygen partial pressure in which the oxygen ion transportation ratio is 1. It is for this reason that the oxygen ion conductor was used as the temperature compensation unit. This idea is completely different from that of the conventional technology. The range of oxygen partial pressure in which the resistance does not depend on oxygen partial pressure is generally wide and is from 1 atm to $10^{-19}$ atm in cerium oxide doped with Gd and from 1 atm to $10^{-30}$ atm in zirconium oxide doped with Ca. Therefore, when those materials are used for the temperature compensation unit, the sensor can be used as the oxygen sensor at the oxygen partial pressure within this range. Furthermore, because the temperature compensation unit is a homogeneous oxygen conductor, rather than a mixture, it has excellent endurance and is easy to produce.

The electrodes have to be porous bodies. The charge carrier in oxygen ion conductors is oxygen ion ($O^{-2}$). In the case of direct current, oxygen ions flow from the negative electrode to the positive electrode. At this time, electrons and oxygen ions from oxygen molecules are generated at the negative electrode.

$$\tfrac{1}{2}O_2 + 2e^- \rightarrow O^{2-}.$$

The generated oxygen ions flow in the oxygen ion conductor and the following reaction proceeds in the positive electrode:

$$O^{2-} \rightarrow \tfrac{1}{2}O_2 + 2e^-.$$

Those reactions proceed on the three-phase boundaries of electrode—gas—oxygen ion conductor. In a porous body, a large number of such three-phase boundaries are present. Therefore, because oxygen ions ($O^{2-}$) flowing in the oxygen ion conductor can be supplied to all of them, the electric resistance does not change. However, when there are few three-phase boundaries, those reactions do not proceed. Therefore, the number of charge carriers is reduced which results in increased electric resistance. In other words, the long-term stability is lost. Therefore, the electrodes in the form of porous bodies is a necessary and sufficient condition for the present invention to be realized.

The second aspect of the present invention will be described below in greater detail.

The resistance-type oxygen sensor in accordance with the present invention is a resistance-type oxygen sensor in which the oxygen gas detection unit is composed from an oxide semiconductor, wherein the oxide semiconductor is an oxide comprising cerium ions and zirconium ions with the concentration of zirconium ions being 0.5–40 mol %, preferably, 5–40 mol %. FIG. 3 shows an example of the structure of resistance-type oxygen sensor in accordance with the present invention. In this sensor, a gas detection unit 3 composed of an oxide semiconductor and a temperature compensation unit 4 for suppressing temperature dependence of the output are arranged on a substrate 1 and an electrode 2 for supplying electricity to the gas detection unit and temperature compensation unit is also arranged therein. However, the structure of the resistance-type oxygen sensor in accordance with the present invention is not limited to that shown in FIG. 3 and can be freely designed according to the object of use.

It is preferred that the oxygen gas detection unit be in the form of a thick film or thin film, but those examples of form are not limiting. No specific limitation is placed on the method for the fabrication of the oxygen gas detection unit. For example, when a thick film is produced, a method can be used by which a film is produced by screen printing. A simple explanation of the process is presented below. An oxide powder comprising cerium ions and zirconium ions is produced in advance. Examples of methods suitable for the fabrication of the powder include a precipitation method and a spray pyrolysis method. Another suitable method comprises mixing cerium oxide and zirconium oxide, solid-phase sintering them at a high temperature of from 1400 to 1700° C., and then grinding the sintered product. The powder obtained is mixed with an organic solvent such as a vehicle to form a paste. The paste thus produced is screen printed on the substrate. The printed product is prefired at a temperature of 400–600° C. and then fired at a temperature of from 1050° C. to 1200° C. to form a thick film. Examples of methods used for film fabrication when a thin film is produced include a MOCVD method, a sputtering method, and a spin coating method. Furthermore, no specific limitation is placed on the starting materials for the fabrication of the oxygen gas detection unit and any materials may be used, provided that the fabricated oxygen gas detection unit is an oxide comprising cerium ions and zirconium ions. In the case of a thick film, the oxygen gas detection unit composed of an oxide semiconductor is preferably in the form of a porous body, that is, a non-dense body.

In the sensor in accordance with the present invention, an electrode is necessary for measuring the resistivity of the oxygen gas detection unit. Examples of materials for the electrode include noble metals such as Pt and Pd, but those examples are not limiting. Further, no specific limitation is placed on the methods for the electrode fabrication.

In the case of a resistance-type oxygen sensor equipped with a heater, which comprises the heater for controlling the temperature of the resistance-type oxygen sensor, for example, a ceramic heater can be mounted on the substrate. No specific limitation is placed on the mounting position, shape, and characteristics of the heater. As a result, the sensor can be warmed to any temperature within a range of 600 to 100° C. even when the temperature of exhaust gases is low.

The oxygen sensor device in accordance with the present invention comprises the resistance-type oxygen sensor in accordance with the present invention, an electric circuit unit, and a display unit for sensor output as the basic structural elements, and can be freely designed by adding a temperature compensation unit, a heater, an appliance capable of applying a constant voltage, and an appliance capable of measuring the voltage. An example of the electric circuit of such a device is shown in FIG. 4. In the figure, the circuit of the heater unit is omitted. The zone surrounded by a dot line represents the resistance-type oxygen sensor. The oxygen gas detection unit and temperature compensation unit serving to suppress the temperature dependence of the output are electrically connected in series, a constant voltage is applied, and the difference in potential in the gas detection unit is read as a sensor output.

The present invention also provides an air/fuel feedback control system for controlling the air/fuel ratio in combustion engines. Here, the air/fuel ratio is the ratio of air and fuel, and there is a one-to-one correspondence between the oxygen partial pressure and air/fuel ratio. In accordance with the present invention, the air/fuel ratio feedback control system for optimizing the combustion efficiency of the combustion engine can be freely designed by employing as the basic structural elements the resistance-type oxygen sensor in accordance with the present invention, a flow meter for measuring the flow rate of air flowing to the combustion engine, a fuel controller for controlling the fuel introduced into the combustion engine, and an electronic control unit for receiving signals from the oxygen sensor and flow meter, conducting calculations, and sending an output signal to the fuel controller.

The air/fuel ratio feedback control system in accordance with the present invention can be employed in an appropriate combustion engine. For example the air/fuel feedback control system for automobiles can be freely designed by employing as the basic structural elements the resistance-type oxygen sensor in accordance with the present invention, a flow meter for measuring the flow rate of air flowing to the engine, a fuel injector for introducing fuel into the engine, and a control circuit for receiving signals from the oxygen sensor and flow meter, conducting calculations, and controlling the fuel injection rate of the fuel injector.

In accordance with the present invention, the system for detecting the exhaust gas catalyst degradation in automobiles can be freely designed by employing as the basic structural elements, for example, the resistance-type oxygen sensor in accordance with the present invention, an electronic control unit for reading the signals from the oxygen sensor and determining as to whether the catalyst has degraded, and a display unit for receiving signals from the electronic control unit and displaying as to whether the catalyst has degraded. The system for detecting the exhaust gas catalyst degradation in automobiles can be widely used in automobiles and combustion engines using a catalyst.

In accordance with the present invention, the responsiveness is greatly improved apparently because the addition of zirconium ions to the gas detection unit composed of cerium oxide, which is an oxide semiconductor, has activated the surface reaction in the surface of oxygen gas detection unit and/or increased the diffusion coefficient of oxygen vacancies. Furthermore, the electron conductivity increases and resistivity of oxygen gas detection unit decreases as the concentration of zirconium ions is increased up to 20 mol %. In cerium oxide, electrons are considered to be moving by hopping on cerium ions. The addition of zirconium ions supposedly increases electron conductivity by decreasing the lattice constant and reducing the electron hopping distance. Furthermore, if the zirconium ion concentration is increased above 20 mol %, the resistivity conversely increases with the increase in zirconium ion concentration. This is supposedly because the increase in the amount of zirconium ions added to cerium oxide reduces the concentration of cerium ions available for electron hopping or increases the amount of precipitated hexagonal crystals.

Furthermore, the addition of zirconium ions increases the dependence of output on the oxygen partial pressure. The reason why the dependence on oxygen partial pressure is small is in a small difference between electron conductivity and oxygen ion conductivity. The addition of zirconium ions increases electron conductivity. As a result, the difference with the oxygen ion conductivity increases and the dependence of the oxygen sensor output on oxygen partial pressure increases.

BEST MODE FOR CARRYING OUT THE INVENTION

The present invention will be described below in greater detail based on the examples thereof, but the present invention is not limited to the below-described examples.

EXAMPLE 1

A fine powder of cerium oxide composite oxide comprising 10 mol % $YO_{1.5}$ was obtained by a precipitation method. A paste in which the fine powder obtained was mixed with an organic solvent vehicle was printed on an aluminum oxide substrate by a screen printing method. Then, heating was conducted in air at a temperature of 500° C., followed by heating in air at a temperature of 1200° C., and a thick film was obtained, this film serving as a temperature compensation unit with a thickness of 20–40 μm and a size of 7 mm×7 mm.

Figure 1:
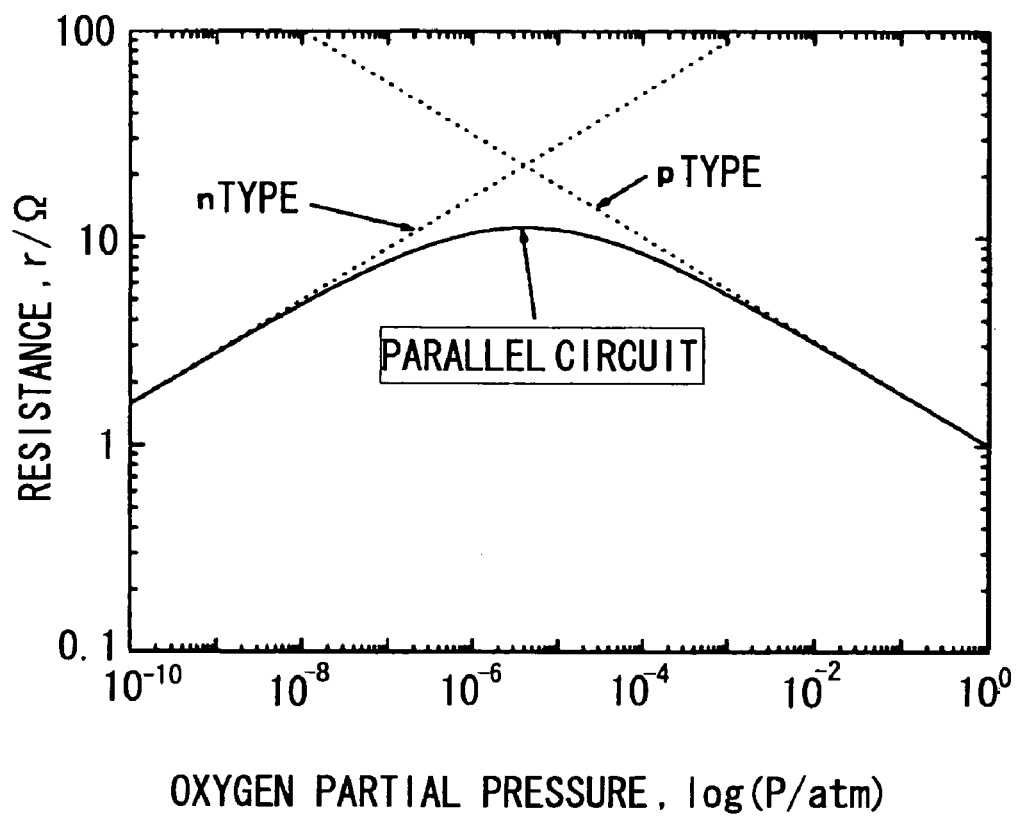
FIG. 1 shows the relationship between the electric resistance of a temperature compensation unit and oxygen partial pressure within the framework of the conventional technology. The results are obtained by conducting calculations with a parallel equivalent circuit.
Figure 2:
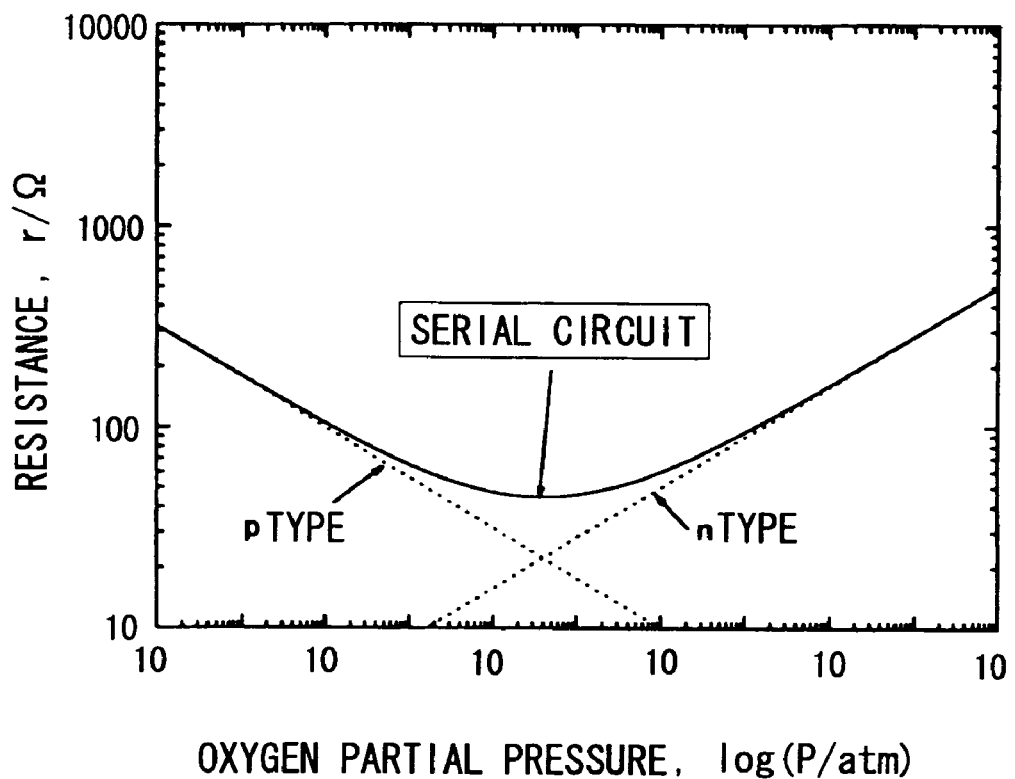
FIG. 2 shows the relationship between the electric resistance of a temperature compensation unit and oxygen partial pressure within the framework of the conventional technology. The results are obtained by conducting calculations with a parallel equivalent circuit.
Figure 3:
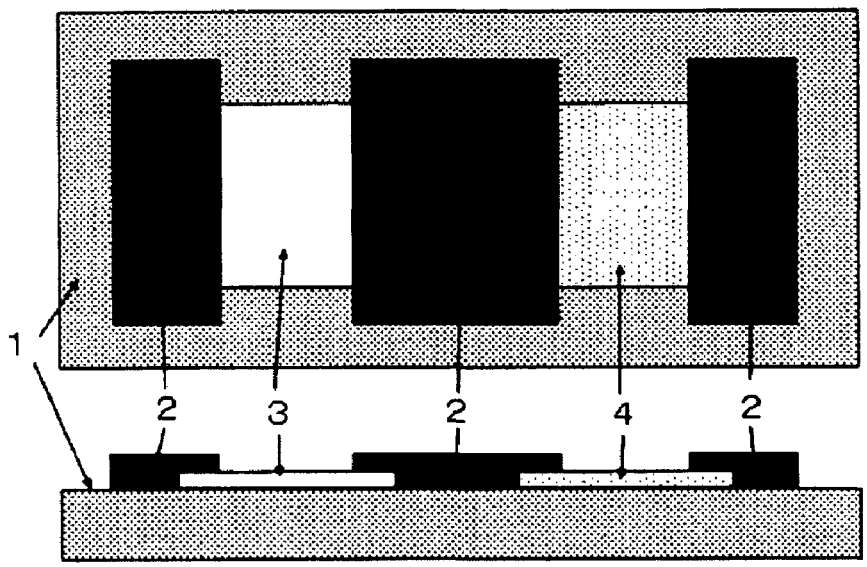
FIG. 3 is a front view and side view illustrating the structure of the resistance-type oxygen sensor in accordance with the present invention.

A paste in which a fine powder of cerium oxide obtained by a spray pyrolysis method was mixed with an organic solvent vehicle was printed by a screen printing method in a series of positions adjacent to the thick film serving as a temperature compensation unit, such as shown in FIG. 3. Then, heating was conducted in air at a temperature of 500° C., followed by heating in air at a temperature of 1200° C., and a thick film was obtained, this film serving as a gas detection unit with a thickness of 20–40 μm and a size of 7 mm×7 mm.

Figure 4:
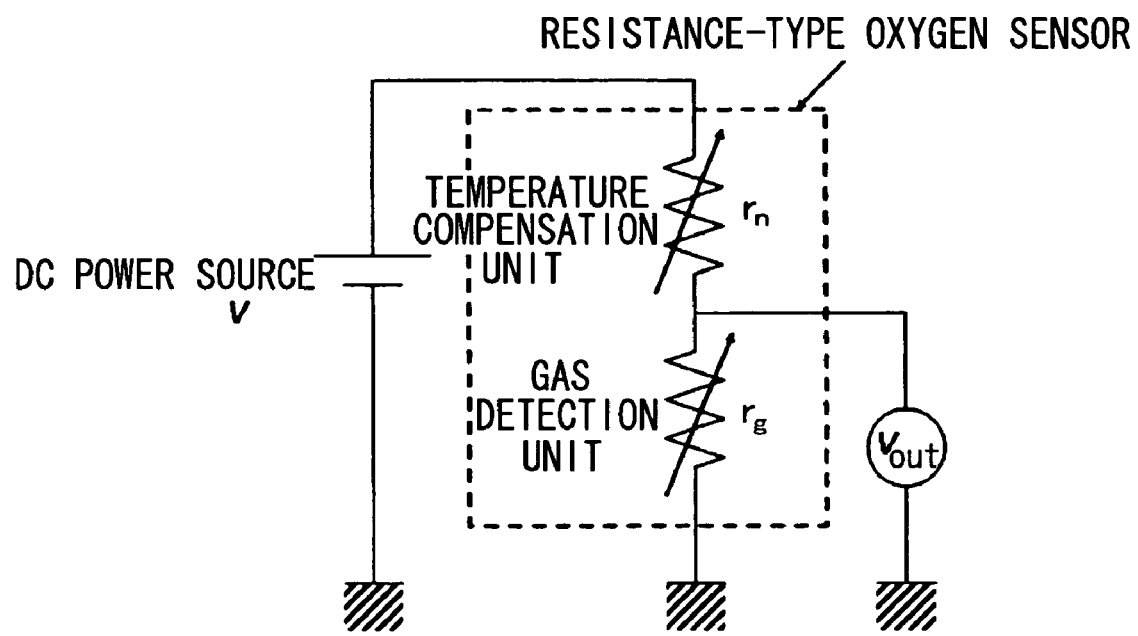
FIG. 4 is a circuit diagram illustrating the operation of the resistance-type oxygen sensor in accordance with the present invention.

A platinum paste (manufactured by Tanaka Noble Metal Industries Co., Ltd.) was coated in a position shown in FIG. 3 and heated at a temperature of 1200° C. to provide a platinum electrode. Observations conducted with a scanning electron microscope showed that the electrode thickness was 10 μm and that the electrode was a porous body. The presence of three-phase boundaries was thereby confirmed. This sensor element was placed in a measurement chamber in which the oxygen partial pressure could be changed, and a DC power source and a voltmeter were connected thereto as shown in FIG. 4. The temperature in an electric furnace was raised to the prescribed level, a voltage V (10 V) was applied by the DC power source, and the difference in potential $V_{out}$ of the gas detection unit was measured.

The results of X-ray diffraction analysis of the gas detection unit showed that the gas detection unit had a single-phase fluorite-type structure. Furthermore, the results of the X-ray diffraction analysis of the temperature compensation unit showed that the temperature compensation unit had a single-phase fluorite-type structure.

Figure 5:
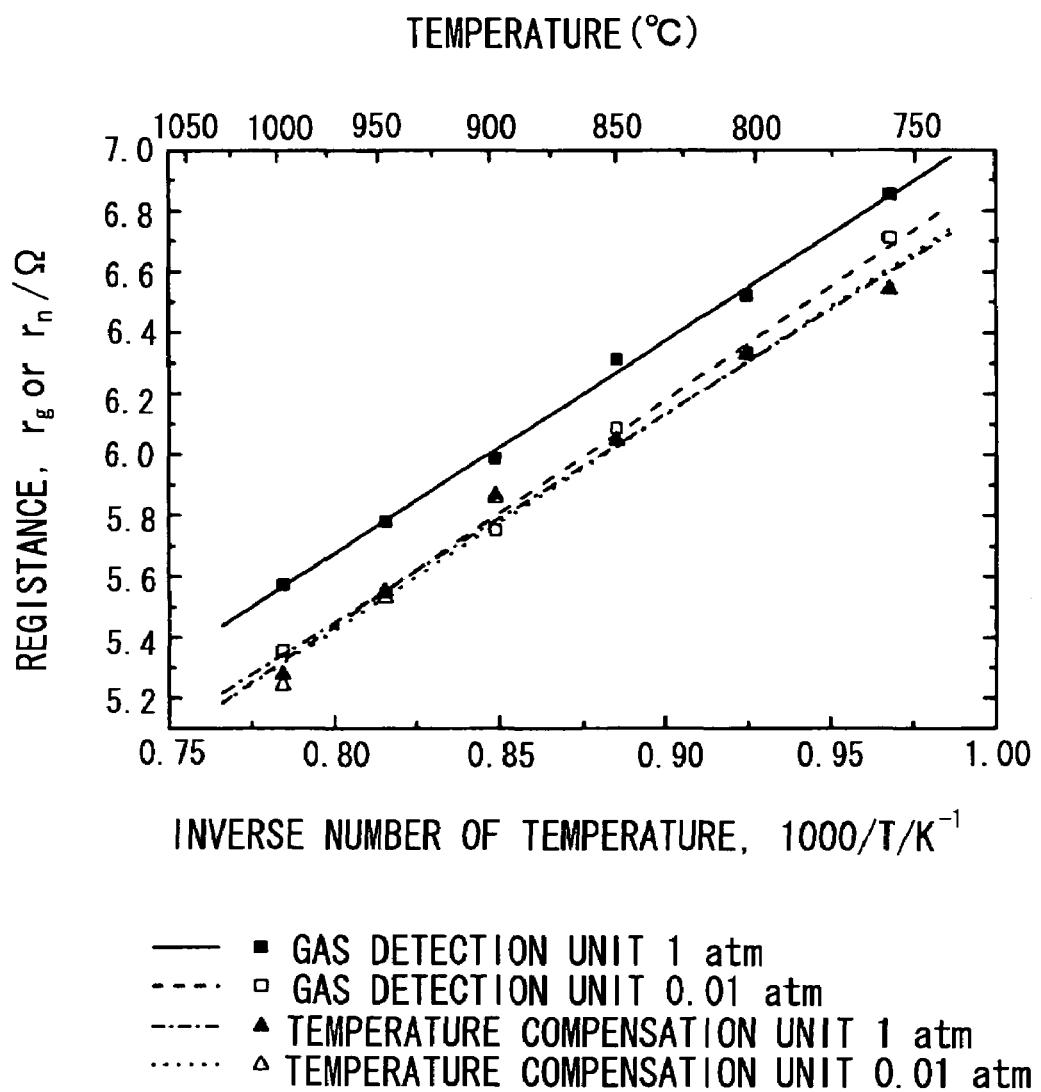
FIG. 5 is a graph illustrating the resistance at an oxygen partial pressure of 1 and 0.01 atm of the gas detection unit and temperature compensation unit of the resistance-type oxygen sensor in accordance with the present invention.

FIG. 5 shows the resistance of the gas detection unit and temperature compensation unit at a temperature of from 750° C. to 1000° C. The temperature dependence of the resistance of the gas detection unit and temperature compensation unit was almost the same. In the gas detection unit, the resistance at 1 atm was significantly different from that at 0.01 atm, but in the temperature compensation unit, the resistance at 1 atm was almost identical to that at 0.01 atm. The results described hereinabove confirmed that in the gas detection unit, the resistance depended on both the temperature and the oxygen partial pressure, in the temperature compensation unit, the resistance depended only on the temperature, and the temperature dependencies of the gas detection unit and temperature compensation unit were almost identical.

Figure 6:
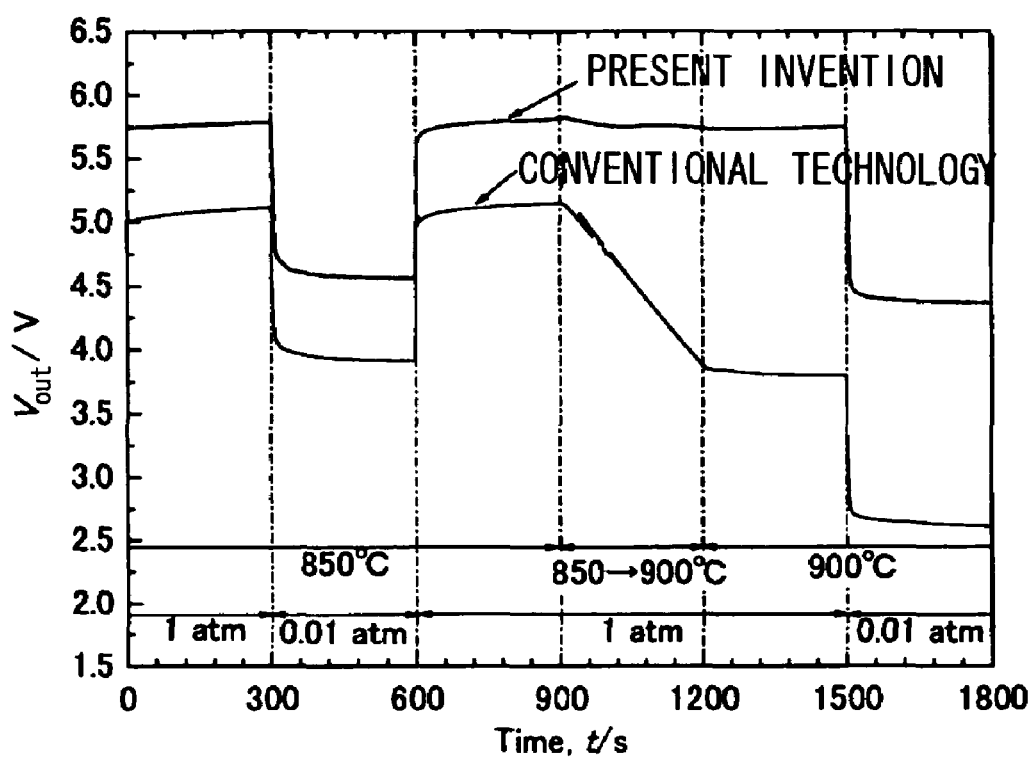
FIG. 6 is a graph representing an example of the output of the resistance-type oxygen sensor in accordance with the present invention and the output of the conventional resistance-type oxygen sensor.
Figure 7:
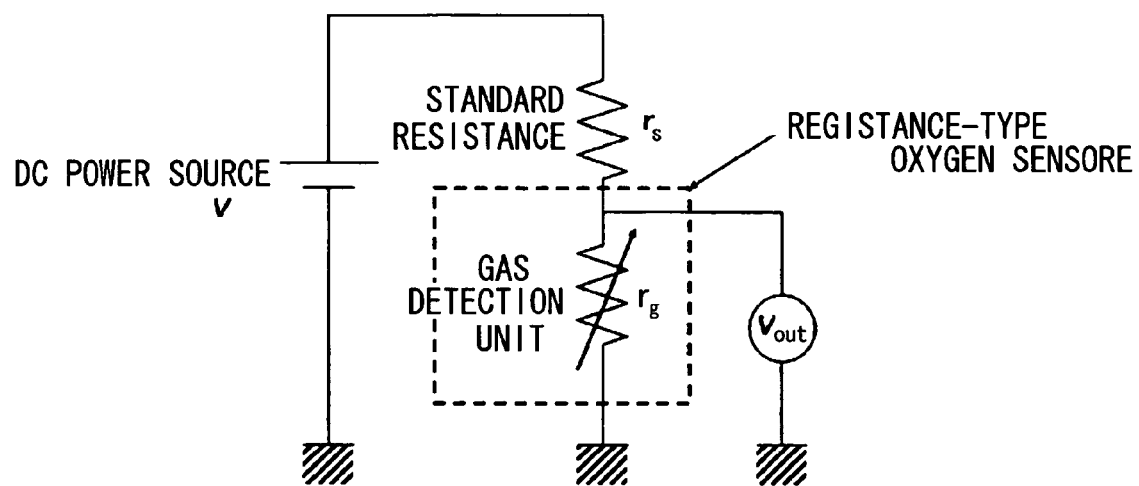
FIG. 7 is a circuit diagram illustrating the operation of the conventional resistance-type oxygen sensor.

FIG. 6 shows an example of the output of the resistance-type oxygen sensor in accordance with the present invention and the output of the conventional resistance-type oxygen sensor. The output of the conventional sensor was obtained with an operation circuit shown in FIG. 7 which used a standard constant resistance. In the conventional sensor, the sensor output at 0.01 atm at a temperature of 850° C. was identical to that at 1 atm at 900° C. and the dependence of the output on temperature was very large. On the other hand, in the sensor in accordance with the present invention, the output at a temperature of 850° C. was practically the same as that at a temperature of 900° C. and the dependence of the output on temperature was found to be small.

Figure 8:
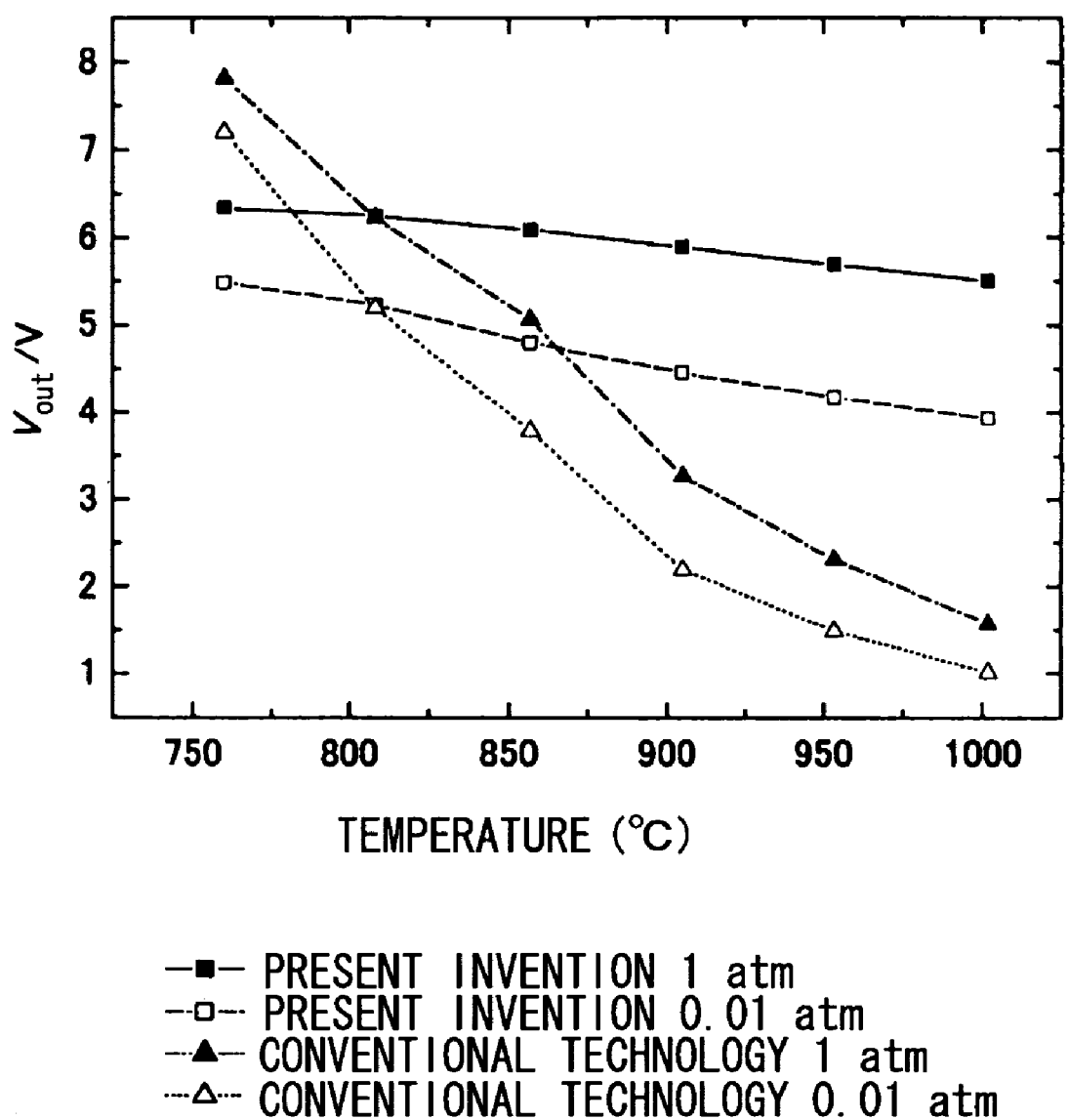
FIG. 8 is a graph illustrating the output of the resistance-type oxygen sensor in accordance with the present invention and the output of the conventional resistance-type oxygen sensor at a temperature of from 750° C. to 1000° C.

FIG. 8 shows the output of the resistance-type oxygen sensor in accordance with the present invention at a temperature of from 750° C. to 1000° C. and the output of the conventional resistance-type oxygen sensor. The output of the conventional resistance-type oxygen sensor was obtained with an operation circuit shown in FIG. 7. The output of the sensor in accordance with the present invention showed a certain small dependence on temperature, but this dependence was found to be significantly less than that of the conventional sensor. Therefore, in accordance with the present invention, it is in principle possible to reduce greatly the dependence on temperature by selecting respective materials for the gas detection unit and temperature compensation unit so that the temperature dependencies thereof are identical.

EXAMPLE 2

Figure 9:
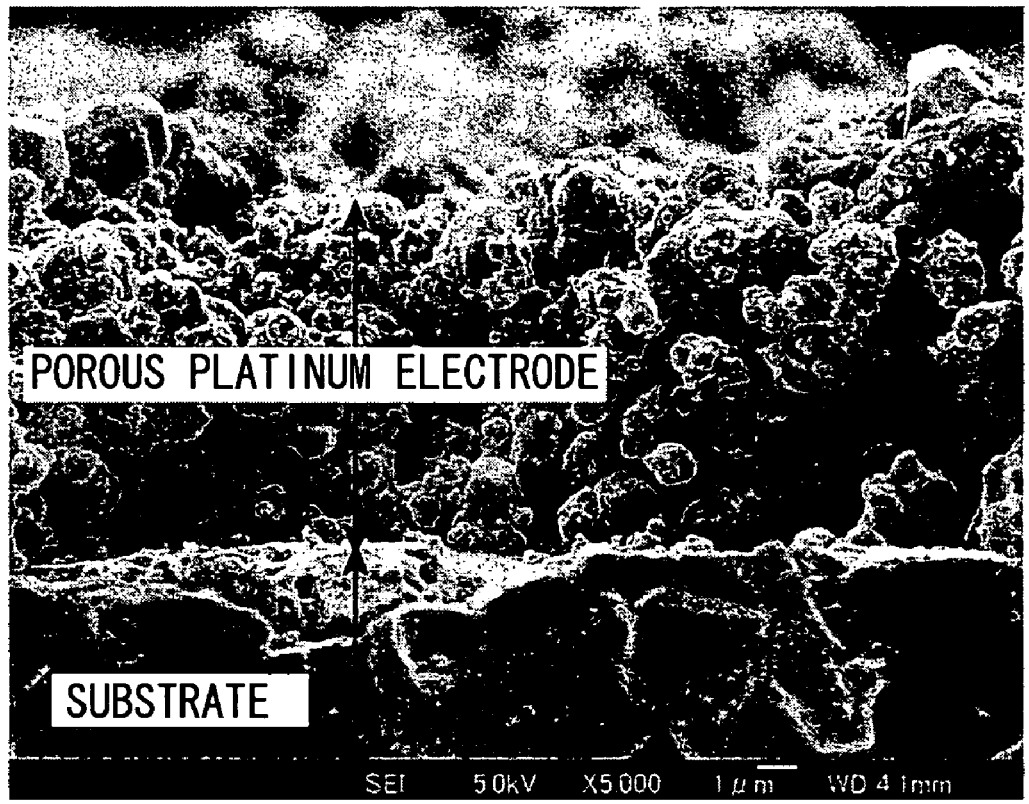
FIG. 9 is a cross-sectional view of a platinum electrode which is in contact with an ion conductor serving as a temperature compensation unit.

FIG. 9 is a cross-sectional view of a platinum electrode which is in contact with an ion conductor serving as a temperature compensation unit. The platinum electrode was obtained by coating a platinum paste (manufactured by Tanaka Noble Metal Industries Co., Ltd.) by a screen printing method, drying at a temperature of 150° C., and then firing for 2 h in air at a temperature of 1200° C. As follows from FIG. 9, the film thickness was about 10 μm and the film was extremely porous.

EXAMPLE 3

An aqueous solution of cerium nitrate and an aqueous solution of zirconium oxynitrate were mixed at the prescribed concentration, the mixed aqueous solution was spray pyrolyzed and a powder composed of fine particles was obtained. The mean particle size of the fine particles was from 200 to 250 nm. A paste in which the powder obtained and an organic solvent vehicle were mixed was printed on an aluminum oxide substrate by a screen printing method. Then, heating was conducted in air at a temperature of 500° C., followed by heating in air at a temperature of 1200° C., and a thick film was obtained.

A platinum electrode was provided by a sputtering method and a sensor was fabricated. The sensor was placed into a measurement chamber in which the oxygen partial pressure could be varied, an electric resistivity between the platinum electrodes was measured by a DC two-terminal method and a sensor characteristic was evaluated. In the present example, the measurements were conducted by a DC two-terminal method, but because the value of the resistance, which was to be measured, was comparatively large, the resistivity obtained was almost equal to that measured by the DC four-terminal method.

Figure 10:
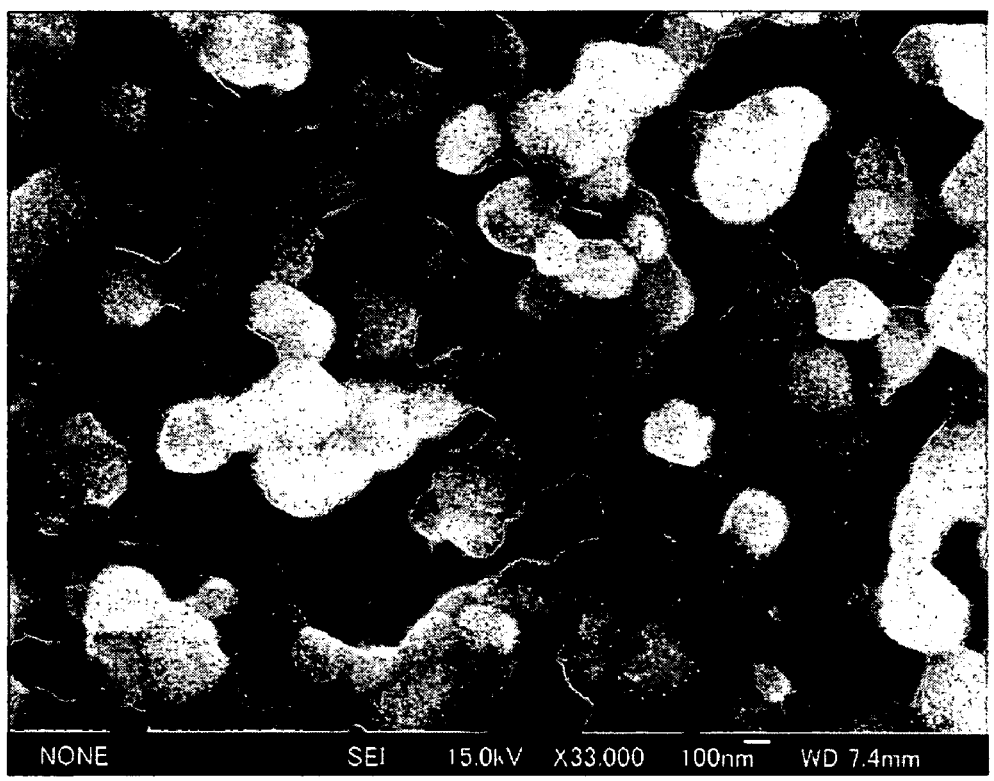
FIG. 10 is a scanning electron microphotograph of a thick film of an oxygen gas detection unit with a zirconium ion concentration of 20 mol %.
Figure 11:
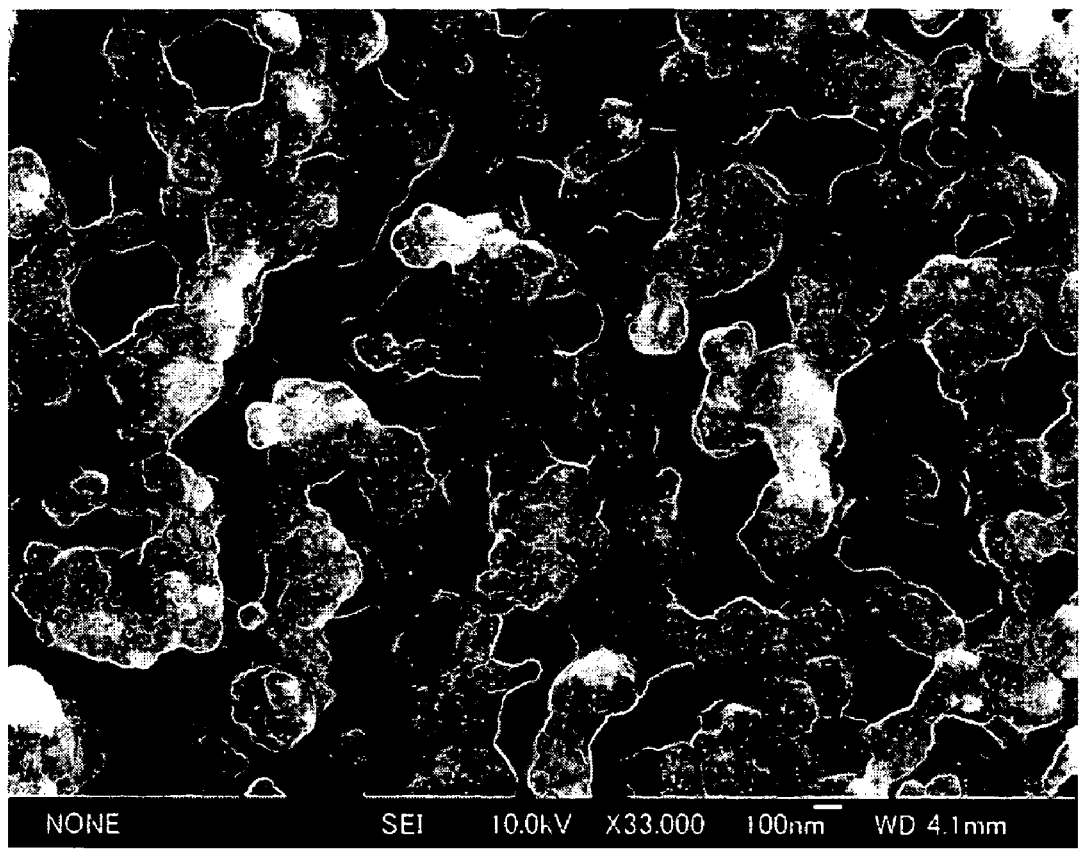
FIG. 11 is a scanning electron microphotograph of a thick film of an oxygen gas detection unit with a zirconium ion concentration of 30 mol %.
Figure 12:
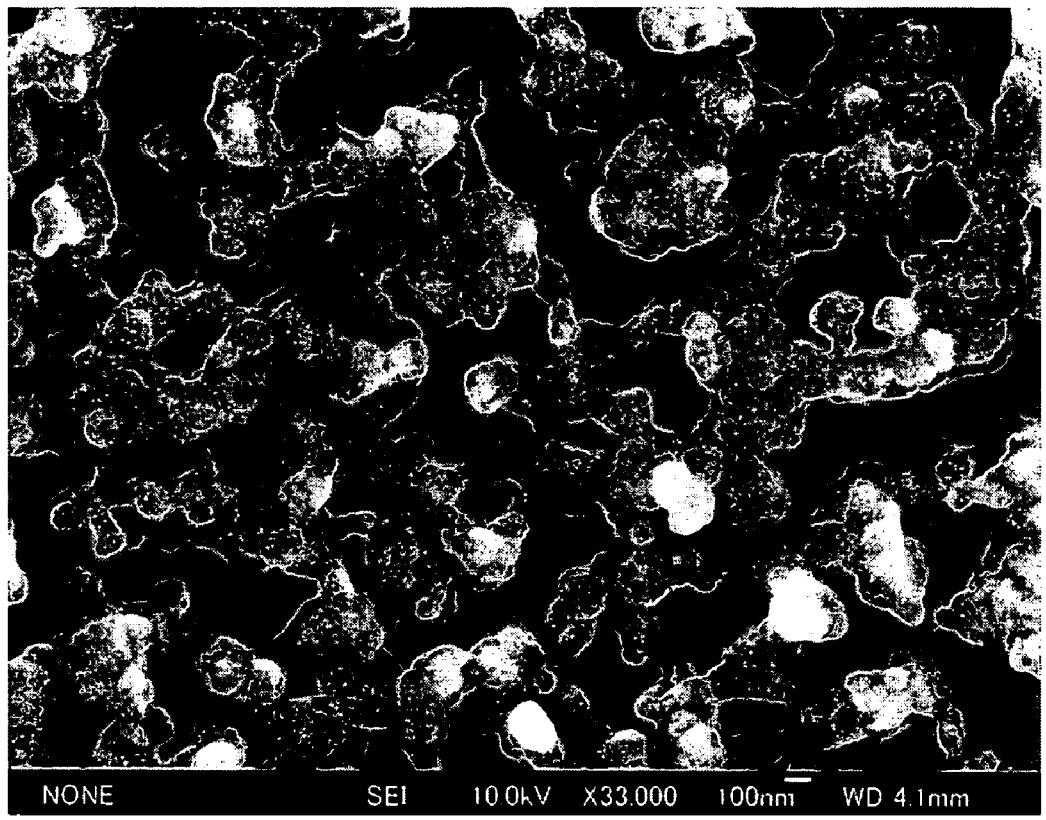
FIG. 12 is a scanning electron microphotograph of a thick film of an oxygen gas detection unit with a zirconium ion concentration of 40 mol %.

FIGS. 10 through 12 show the results obtained in observing the structure of the thick film after firing at a temperature of 1200° C. with a scanning electron microscope. FIGS. 10, 11, and 12 show the scanning electronograms of the thick films with a zirconium ion concentration of 20, 30, and 40 mol %, respectively. For the films in which the zirconium ion concentration was less than 20 mol %, the structure was almost identical, the grain size was 200 nm, and the films were extremely porous. At a zirconium ion concentration of 30 and 40 mol %, fine grains were observed. This is apparently due to the below-described tetragonal structure. The results of X-ray diffraction analysis of the thick films after firing demonstrated that at a zirconium ion concentration of 0.5 to 20 mol %, there was a single-phase cubic structure. However, at 30 mol % or more, there was a two-phase mixture of tetragonal and cubic crystals. The peak angle and intensity ratio ($I_t/I_c$, where $I_t$ and $I_c$ are the peak intensities of (111) planes of the cubic crystal and tetragonal crystal, respectively) of the cubic crystal and tetragonal crystal area shown in Table 1. At a zirconium ion concentration from 0 to 20 mol %, the plane angle of the (111) plane of the cubic crystal increased monotonously. This result indicates that the lattice constant of the cubic crystal decreased monotonously. At a zirconium ion concentration of 30 mol % or more, the angle was not changed in both the cubic crystals and tetragonal crystals, but the intensity ratio of the tetragonal crystals increased with the increase in the amount of ions added. This indicates that the ratio of tetragonal crystals increased.

TABLE 1

| Zirconium ion concentration (mol %) | Cubic crystal (111) Angle (2θ/°) | Tetragonal crystal (111) Angle (2θ/°) | Intensity ratio $I_t/I_c$ |
|---|---|---|---|
| 0 | 28.52 | | |
| 0.5 | 28.56 | | |
| 1 | 28.58 | | |
| 2 | 28.60 | | |
| 5 | 28.64 | | |
| 10 | 28.78 | | |
| 20 | 28.84 | | |
| 30 | 28.92 | 29.92 | 0.08 |
| 40 | 28.92 | 29.92 | 0.19 |
| 60 | 28.92 | 29.90 | 1.02 |

Further, the resistivity of the oxygen gas detection unit of the aforementioned sensors at various temperatures is shown in Table 2. The resistivity of the sample having no zirconium ions added thereto (addition-free sample: conventional product) is denoted by $\rho_0$, and the normalized resistivity $\rho/\rho_0$ is shown in Table 3. The measurement atmosphere had a partial oxygen pressure of 1 atm and the film thickness was the same for all the samples. Due to addition of 0.5 mol % of zirconium ions, the resistivity in a range from 600° C. to 800° C. decreased to about 50% that without the addition. Up to a zirconium ion concentration of 20 mol %, resistivity increased with the concentration of zirconium ions. The resistivity of the oxygen gas detection unit having zirconium ions added thereto at 10–30 mol % decreased to about 20 mol % the resistivity without the addition. In this addition concentration range, the resistivity at a temperature of 800° was 20 Ωm or less.

TABLE 2

| Zirconium ion concentration (mol %) | ρ (Ωm) | | | | |
|---|---|---|---|---|---|
| | 600° C. | 700° C. | 800° C. | 900° C. | 1000° C. |
| 0 | 2560 | 530 | 121 | 28.6 | 7.02 |
| 0.5 | 1380 | 258 | 57.5 | 15.8 | 7.23 |
| 1 | 1040 | 205 | 53.8 | 17.6 | 6.69 |
| 2 | 1088 | 211 | 47.0 | 12.5 | 5.56 |
| 5 | 829 | 136 | 26.4 | 6.71 | 2.14 |
| 10 | 479 | 77.1 | 15.4 | 4.15 | 1.67 |
| 20 | 443 | 54.2 | 9.31 | 2.28 | 0.75 |
| 30 | 580 | 74.9 | 13.6 | 3.18 | 1.30 |
| 40 | 1130 | 175 | 31.4 | 7.39 | 2.09 |
| 50 | 1530 | 258 | 51.5 | 13.8 | 7.63 |
| 60 | 1250 | 335 | 91.9 | 40.0 | 15.3 |

TABLE 3

| Zirconium ion concentration (mol %) | $\rho/\rho_0$ | | | | |
|---|---|---|---|---|---|
| | 600° C. | 700° C. | 800° C. | 900° C. | 1000° C. |
| 0 | 1 | 1 | 1 | 1 | 1 |
| 0.5 | 0.536 | 0.486 | 0.472 | 0.551 | 1.029 |
| 1 | 0.405 | 0.387 | 0.441 | 0.617 | 0.953 |
| 2 | 0.424 | 0.398 | 0.386 | 0.437 | 0.793 |
| 5 | 0.323 | 0.257 | 0.216 | 0.235 | 0.305 |
| 10 | 0.187 | 0.145 | 0.126 | 0.145 | 0.237 |
| 20 | 0.173 | 0.102 | 0.076 | 0.080 | 0.107 |
| 30 | 0.226 | 0.141 | 0.112 | 0.111 | 0.185 |
| 40 | 0.439 | 0.33 | 0.257 | 0.259 | 0.0297 |
| 50 | 0.595 | 0.486 | 0.423 | 0.481 | 1.086 |
| 60 | 0.488 | 0.632 | 0.754 | 1.400 | 2.173 |

The dependence of the aforementioned sensors on the oxygen partial pressure at various temperatures is shown in Table 4. Here, n is a variable satisfying the relationship in which $\rho$ is proportional to $P^{1/n}$, and the smaller is this value, the larger is the dependence on the oxygen partial pressure. When 5 mol % was added, the value of n reduced with respect to that of the sample without the addition at all the temperatures within a range from 600 to 1000°. When 20 to 40 mol % was added, the value of n was within a range of 4 to 6 at all the temperatures.

TABLE 4

| Zirconium ion concentration (mol %) | n ($\rho \propto P^{1/n}$) | | | | |
|---|---|---|---|---|---|
| | 600° C. | 700° C. | 800° C. | 900° C. | 1000° C. |
| 0 | 11.7 | 9.0 | 7.3 | 6.4 | 6.3 |
| 0.5 | 8.2 | 7.4 | 7.1 | 6.7 | 7.0 |
| 1 | 11.5 | 8.9 | 7.7 | 7.4 | 7.5 |
| 2 | 7.8 | 7.2 | 6.7 | 6.8 | 7.5 |
| 5 | 6.0 | 5.4 | 5.4 | 5.7 | 6.1 |
| 10 | 6.1 | 5.4 | 5.2 | 5.8 | 6.2 |
| 20 | 4.7 | 4.5 | 4.6 | 4.9 | 5.4 |
| 30 | 4.9 | 4.6 | 4.8 | 5.1 | 5.3 |
| 40 | 5.6 | 5.0 | 5.0 | 5.5 | 5.7 |
| 50 | 6.6 | 5.7 | 5.6 | 5.8 | 6.7 |
| 60 | 47.5 | 27.9 | 17.5 | 20.7 | 20.9 |

Table 5 shows the response time during switching of the oxygen partial pressure in the aforementioned sensor from 1 atm to 0.01 atm at various temperatures. The response time is defined as the time required for the resistivity to change as $0.9(\rho_s-\rho_\infty)$ after the oxygen partial pressure has been changed, wherein $\rho_s$ stands for the resistivity before the oxygen partial pressure has been changed and $\rho_\infty$ stands for a stabilized resistivity after the oxygen partial pressure has been switched. At a temperature of 600° C., the addition of 0.5 mol % greatly shortened the response time and the response time decreased as the amount added was increased up to 5 mol %. No changes in response time were observed after the addition of 5 mol % or more, and the response time was about 11 sec at 600° C. and about 5 sec at 700° C. to 1000° C. The difference in response between the material without the additive and the material having zirconium ions added thereto was not detected at 900° C. and 1000° C. Therefore, the response time at a temperature of 800° C. and 900° C. was evaluated with a separate test device. This is shown in the below-described Example 3.

TABLE 5

| Zirconium ion concentration (mol %) | Response time, $t_{90}$/sec | | | | |
|---|---|---|---|---|---|
| | 600° C. | 700° C. | 800° C. | 900° C. | 1000° C. |
| 0 | 42 | 16 | 11 | 7 | 6 |
| 0.5 | 22 | 11 | 9 | 7 | 5 |
| 1 | 17 | 13 | 10 | 8 | 7 |
| 2 | 14 | 14 | 8 | 7 | 6 |
| 5 | 10 | 5 | 5 | 4 | 4 |
| 10 | 10 | 8 | 7 | 7 | 7 |
| 20 | 11 | 6 | 6 | 7 | 6 |
| 30 | 11 | 7 | 6 | 6 | 6 |
| 40 | 12 | 6 | 5 | 4 | 4 |
| 50 | 9 | 8 | 7 | 6 | 7 |
| 60 | 13 | 8 | 9 | 9 | 6 |

The results presented above demonstrated that when the zirconium ion concentration was from 0.5 to 40 mol %, the response time, resistivity, and dependence on the oxygen partial pressure were improved with respect to those of the conventional product (resistance-type oxygen sensor having no cerium oxide added thereto). Furthermore, when the zirconium ion concentration was from 5 to 40 mol %, the resistivity was lower and response time was shorter than those of the conventional product, and the factor n representing the dependence on the oxygen partial pressure was within a range of 4–7. Furthermore, when the zirconium ion concentration was from 10 to 30 mol %, the response time was about 1 sec at 600° C. and about 5 sec at 700° C. to 1000° C., the resistivity at 800° C. was 20 Ωm or less, and the factor n representing the dependence on the oxygen partial pressure was within a range of 4 to 6, that is, especially good characteristics were obtained.

EXAMPLE 4

A sensor was fabricated in the same manner as in Example 3, except that the firing temperature was changed to 1100° C. When the structure of the thick film was observed under a scanning electron microscope, the mean grain size was almost identical to that of Example 3, but the size of the neck connecting a grain to a grain was smaller than that of Example 3. As shown in Table 6, the resistivity of the sample with a zirconium ion concentration of 20 mol % was slightly larger than that of Example 1, but smaller than that of the conventional product. The value of n representing the dependence on the oxygen partial pressure was from 4 to 5.6 and, similarly to Example 3, the dependence on the oxygen partial pressure was improved with respect to that of the additive-free conventional product. The response time was also improved with respect to that of the conventional product. Therefore, the effect of zirconium oxide addition was confirmed even when the firing temperature was changed.

TABLE 6

| Temperature (° C.) | $\rho$/Ωm | | n ($\rho \propto P^{1/n}$) | | $t_{90}$/sec | |
|---|---|---|---|---|---|---|
| | 20 mol % | 0 mol % | 20 mol % | 0 mol % | 20 mol % | 0 mol % |
| 600 | 666 | 5260 | 5.65 | 12.05 | 8.5 | 14.0 |
| 700 | 82.9 | 706 | 4.63 | 9.35 | 7.0 | 7.0 |
| 800 | 14.9 | 153 | 4.59 | 7.19 | 6.0 | 7.0 |
| 900 | 3.66 | 38.9 | 4.83 | 6.37 | 6.0 | 6.5 |
| 1000 | 1.17 | 11.1 | 5.35 | 5.88 | 6.0 | 7.0 |

EXAMPLE 5

A response time was examined with a high-speed response evaluation device with respect to an oxygen sensor with a zirconium ion concentration of 20 mol % that was used in Example 3 and an oxygen sensor without the addition of zirconium. The high-speed response evaluation device makes it possible to change the entire pressure in the sensor measurement chamber at a high speed, uses air and the atmosphere in the measurement chamber, has an oxygen partial pressure, for example, equal to the total pressure multiplied by 0.21, and can change the oxygen partial pressure at a high speed. Furthermore, the time required for changing the oxygen partial pressure is 20 msec or less and the oxygen partial pressure can be changed at a very high speed. In this test example, the atmosphere in the measurement chamber was air and the total pressure was changed from 3 atm to 1 atm and then from 1 atm to 3 atm. Thus, the oxygen partial pressure was changed from 0.6 atm to 0.2 atm or from 0.2 atm to 0.6 atm. The response time of the sensor (defined as in Example 3) was evaluated at a temperature of 800° C. and 900° C. The results are shown in Table 7. The response time of the sensor having zirconium ions added thereto was shorter that that of the addition-free sensor at all temperatures and all changes of the oxygen partial pressure. The addition of zirconium ions greatly improved the response time at both 800° C. and 900° C.

TABLE 7

| | Response time ($t_{10/ms}$) | | | |
|---|---|---|---|---|
| | Zirconium ion concentration: 0 mol % | | Zirconium ion concentration: 20 mol % | |
| Temperature | 0.6 atm → 0.2 atm | 0.2 atm → 0.6 atm | 0.6 atm → 0.2 atm | 0.2 atm → 0.6 atm |
| 800° C. | 178 | 124 | 132 | 80 |
| 900° C. | 37 | 22 | 29 | 13 |

INDUSTRIAL APPLICABILITY

As described hereinabove, the present invention relates to a resistance-type oxygen sensor and to an oxygen sensor device and air/fuel ratio control system using the sensor. The following effects can be demonstrated with the present invention.

(1) With the conventional resistance-type oxygen sensors, the dependence of temperature was very high and the sensor temperature had to be controlled with an extremely high accuracy. However, in the sensor in accordance with the present invention, even if the temperature is somewhat changed, practically no effect is produced on the sensor output. Therefore, the level of requirements placed on temperature control can be lowered.

(2) Because the temperature compensation unit is a single phase, rather than a mixture, the fabrication process is simple. Because no glass seal is used, the resistance to thermal shocks and endurance are high.

(3) The sensor can be used as an oxygen sensor in a wide range of oxygen partial pressure.

(4) Due to the addition of metal ions, cerium oxide becomes an oxide semiconductor (electron conductor) or an oxygen ion conductor. Therefore, with the present invention, the gas detection unit and temperature compensation unit can be the materials comprising cerium oxide as the main components.

(5) Cerium oxide has high endurance with respect to corrosive gases. Therefore, in accordance with the present invention, when cerium oxide is used as the main component, a resistance-type oxygen sensor with excellent long-term stability can be obtained.

Furthermore, another specific feature of the present invention is that in a resistance-type oxygen sensor in which an oxygen gas detection unit is composed of an oxide semiconductor, the oxide semiconductor is an oxide comprising cerium ions and zirconium ions and the zirconium ion concentration is 0.5–40 mol %, and the present invention makes it possible to obtain the following effects.

(6) A resistance-type oxygen sensor having improved performance can be provided.

(7) The response time of the sensor can be shortened significantly.

(8) At the same time, the resistivity of the oxygen gas detection unit can be reduced and dependence of the oxygen partial pressure can be increased.

(9) An oxygen sensor device and an air/fuel ratio control system comprising the aforementioned sensor can be provided.

The invention claimed is:

1. A resistance-type oxygen sensor with suppressed temperature dependence, comprising:
   (1) a gas detection unit composed of an oxide semiconductor with a resistance value varying according to temperature and an oxygen partial pressure of atmospheric gas and a temperature compensation unit composed of a conductor with suppressed dependence of a resistance value on oxygen partial pressure are connected in series;
   (2) said conductor is an oxygen ion conductor; and
   (3) an electrode for electric contact with said temperature compensation unit is exposed to the atmospheric gas and is a porous body.

2. The resistance-type oxygen sensor according to claim 1, wherein a unit with a temperature dependence similar to that of the gas detection unit is used as said temperature compensation unit.

3. The resistance-type oxygen sensor according to claim 1, wherein a unit with a temperature dependence identical to that of the gas detection unit is used as said temperature compensation unit.

4. The resistance-type oxygen sensor according to claim 1, wherein the oxide semiconductor, which is said gas detection unit, is cerium oxide or a composite oxide comprising cerium oxide as the main component.

5. The resistance-type oxygen sensor according to claim 1, wherein the oxygen ion conductor, which is said temperature compensation unit, is a composite oxide comprising cerium oxide as the main component.

6. An oxygen sensor device comprising the resistance-type oxygen sensor according to any one of claims 1 to 5 as a structural element.

7. The oxygen sensor device according to claim 6, comprising means for applying a constant voltage and means for measuring a voltage.

8. An air/fuel ratio feedback control system for controlling the air/fuel ratio of a combustion engine, which comprises the resistance-type oxygen sensor according to any one of claims 1 to 5 as a structural element.

9. The air/fuel ratio feedback control system according to claim 8, which controls the air/fuel ratio for automobiles.

10. A system for detecting the automobile exhaust gas catalyst degradation, which comprises the resistance-type oxygen sensor according to any one of claims 1 to 5 as a structural element.

11. A resistance-type oxygen sensor comprising an oxygen gas detection unit composed of an oxide semiconductor and a substrate as structural elements,
   wherein the oxide semiconductor is an oxide comprising cerium ions and zirconium ions and the ratio of amount of substance of zirconium ions to a sum total of amount of substance of cerium ions and zirconium ions is 0.5–40 mol %, and
   wherein a resistance value at a temperature of 800° C. is 20 Ωm or less, and resistivity is proportional to 1/n power of oxygen partial pressure at a temperature of from 600° C. to 900° C., where n is a number from 4 to 5.5.

12. The resistance-type oxygen sensor according to claim 11, wherein the ratio of amount of substance of zirconium ions to a sum total of amount of substance of cerium ions and zirconium ions is 5–40 mol %.

13. The resistance-type oxygen sensor according to any one of claims 11 and 12, wherein the oxygen gas detection unit composed of an oxide semiconductor is a porous thick film.

14. The resistance-type oxygen sensor according to any one of claims 11 and 12, comprising a temperature compensation unit for suppressing the dependence of output on temperature, the temperature compensation unit being electrically connected in series to the oxygen gas detection unit.

15. An oxygen sensor device comprising the resistance-type oxygen sensor according to any one of claims 11 and 12 as a structural element.

16. The oxygen sensor device according to claim 15, comprising an appliance for applying a constant voltage and an appliance for measuring a voltage.

17. An air/fuel ratio feedback control system for controlling the air/fuel ratio of a combustion engine, which comprises the resistance-type oxygen sensor according to any one of claims 11 and 12 as a structural element.

18. An air/fuel feedback control system according to claim 17, wherein the combustion engine is a combustion engine for an automobile.

19. A system for detecting the automobile exhaust gas catalyst degradation, which comprises the resistance-type oxygen sensor according to any one of claims 11 and 12.

* * * * *